United States Patent

Hansen et al.

[11] Patent Number: 5,719,312
[45] Date of Patent: Feb. 17, 1998

[54] PROCESS FOR THE PREPARATION OF 5-FORMYLVALERIC ACID AND 5-FORMYLVALERATE ESTER

[75] Inventors: Carolina B. Hansen, Sittard; Johannes G. de Vries, Maastricht, both of Netherlands

[73] Assignee: DSM N.V., Heerlen, Netherlands

[21] Appl. No.: 671,929

[22] Filed: Jun. 27, 1996

Related U.S. Application Data

[63] Continuation of PCT/NL94/00324, Dec. 23, 1994.

[30] Foreign Application Priority Data

Dec. 30, 1993 [BE] Belgium ................... 9301483

[51] Int. Cl.⁶ ..................... C07C 69/66; C07C 59/147
[52] U.S. Cl. ..................................................... 560/177
[58] Field of Search ........................... 560/177; 562/577

[56] References Cited

U.S. PATENT DOCUMENTS 5,264,616  11/1993  Roeper et al. ................... 560/175

FOREIGN PATENT DOCUMENTS 0 518 241  12/1992  European Pat. Off.
0 556 681   8/1993  European Pat. Off.

*Primary Examiner*—Paul J. Killos
*Assistant Examiner*—Rosalynd A. Keys
*Attorney, Agent, or Firm*—Cushman Darby & Cushman IP Group of Pillsbury Madison & Sutro, LLP

[57] ABSTRACT

The invention relates to a process for the preparation of 5-formylvaleric acid or the corresponding 5-formylvalerate by hydroformylation of 3-pentenoic acid or 3-pentenoate ester with carbon monoxide and hydrogen in the presence of a catalyst comprising of rhodium and a phosphite ligand, wherein the phosphite ligand is represented by the following general formula

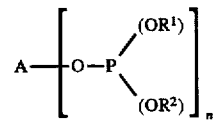

where $R^1$ and $R^2$ are the same or different aromatic organic groups and where A is an n-valent group or atom and where n is an integer chosen upwards of 2 and where the respective $[-O-P(OR^1)(OR^2)]$ group may be the same group or different groups and where the phosphite forms a chelate-type complex with rhodium.

7 Claims, No Drawings

PROCESS FOR THE PREPARATION OF 5-FORMYLVALERIC ACID AND 5-FORMYLVALERATE ESTER

This application claims priority to Belgian Application 9301483, filed Dec. 30, 1993 and is a continuation of PCT/NL94/00324, filed Dec. 23, 1994.

The invention relates to a process for the preparation of 5-formylvaleric acid or the corresponding 5-formylvalerate ester by hydroformylation of 3-pentenoic acid or 3-pentenoate ester with carbon monoxide and hydrogen in the presence of a catalyst system comprising rhodium and a phosphite ligand.

Hydroformylation here means reacting an unsaturated hydrocarbon compound with carbon monoxide and hydrogen in the presence of a catalyst, in which process an aldehyde is prepared.

Such a process is disclosed in EP-A-556681. That patent specification describes a process in which methyl 3-pentenoate is hydroformylated to the linear methyl 5-formylvalerate. The catalyst employed in this process is comprised of rhodium and a bidentate phosphite ligand of the formula (1):

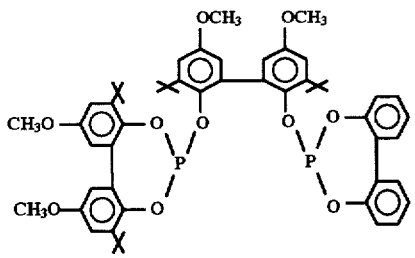

in which + is a tert-butyl group. According to EP-A-5561681 the highest selectivity to the methyl 5-formylvalerate which can be reached is 76.7 mol %. Selectivity is calculated as the molar amount of the specific product relative to the molar amount of converted 3-pentenoate ester (or acid).

Disadvantages of the process of EP-A-556681 are that the selectivity towards the 5-formylvalerate ester is low and that the organic phosphite ligands are as a rule difficult to prepare.

The object of the present invention is a process in which 3-pentenoic acid or 3-pentenoate ester can be hydroformylated in the presence of a catalyst comprising rhodium and an easy to prepare organic phosphite ligand, enabling the linear 5-formylvaleric acid or 5-formylvalerate ester to be prepared with a high selectivity.

This object is achieved in that the phosphite ligand is represented by the following general formula (2),

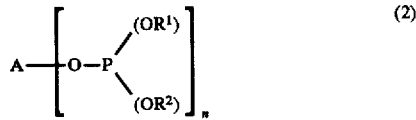

where $R^1$ and $R^2$ are the same or different monovalent aromatic organic groups and where A is an n-valent group or atom and where n is an integer of at least 2 and where the respective [—O—P($OR^1$)($OR^2$)] group may be the same group or different groups and where the phosphite forms a chelate-type complex with rhodium.

It has been found that the 5-formylvaleric acid (ester) is prepared with high selectivity when 3-pentenoic acid (or 3-pentenoate ester) is hydroformylated by the process according to the invention.

An added advantage, in case 5-formylvalerate ester is the desired product, is that less 4-formylvalerate ester relative to 3-formyl valerate is prepared than in the process according to EP-A-556681. This is advantageous because the 4-formylvalerate ester has almost the same boiling point as the 5-formylvalerate ester: a smaller amount of 4-formylvalerate ester allows simpler distillative separation of these two components. Moreover, less 3- and 4-formylvalerate ester are prepared in the process according to the invention, so that distillative separation of the 3-, 4- and 5-formylvalerates ester can be effected even simpler.

A further advantage is that the bidentate phosphite ligands according to formula (2) can be prepared with a more simple process than the bidentate phosphite ligands exemplified in EP-A-556681. As a rule the ligands according to formula (2) can be prepared in at least one synthesis step less than the bidentate phosphite ligands according to EP-A-556681. Especially the bidentate phosphite ligands according to formula (2) which are symmetrical (the different —($OR^1$) ($OR^2$) groups being the same) are more simple to prepare. Furthermore bidentate phosphite ligands which do not need to be synthesized starting from a substituted bisphenol are also more simple to prepare. This is because the substituted bisphenol is as a rule not readily available and will have to be synthesized separately. The bidentate phosphite ligand according to formula (1) is an example of a compound which is prepared starting from two different substituted bisphenols. Furthermore the bidentate phosphite ligand according to formula (1) is not symmetrical. The large number of synthesis steps required for preparing a ligand according to formula (1) is for example described in U.S. Pat. No. 4,748,261.

By a chelate-type complex is meant that (substantially) at least two phosphorous P atoms of a phosphite-group-containing molecule form a coordinated bond with one rhodium atom/ion. By a non-chelate-type complex is meant that substantially only one phosphorous P atom of a phosphite-group-containing molecule forms a coordinated bond with one rhodium atom/ion. The choice of the organic group A of the ligand according to formula (2) will determine whether a chelate-type complex of the phosphite ligand and rhodium is formed.

A hydroformylation process which uses a catalyst system resembling the catalyst system according to the invention is disclosed in EP-A-518241. EP-A-518241 teaches, however, that catalyst systems comprising phosphites which form a chelate-type complex with rhodium are suitable fox hydroformylation of terminally unsaturated olefins, whilst phosphites that do not form a chelate-type complex (non-chelate-type) are suitable for hydroformylating branched internally unsaturated olefins to aldehydes with high selectivity. It is thus surprising that when starting from an internally unsaturated 3-pentenoate ester and using phosphites that form a chelate-type complex with rhodium, a high selectivity towards 5-formylvalerate can be obtained.

The process according to the invention is carried out in the presence of a catalyst comprising a phosphite of formula (2), where $R^1$ and $R^2$ are the same or different aromatic organic groups with preferably 6 to 30 carbon atoms. Examples of suitable aromatic organic groups are phenyl, naphthyl, antryl or phenantryl. The phenyl and the β-naphthyl group are preferably applied since phosphites with these groups are readily obtainable. The groups $R^1$ and $R^2$ are not connected to each other in any way other than via the phosphorous atom P.

Preferably, the aromatic hydrocarbon group(s) $R^1$ and/or $R^2$ is/are substituted with a group other than a hydrogen atom on at least one carbon atom immediately adjacent to the carbon atom that is bonded with the oxygen atom (from the —O—P(—O—)$_2$ group (hereafter referred to as ortho-substituted). These phosphites have been found to possess a good stability. Most preferably, $R^1$ and $R^2$ are both ortho-substituted. As a rule, the substituent is an organic group. Examples of suitable organic groups that may serve as substituent are $C_1$-$C_{20}$ alkyl groups, $C_6$-$C_{20}$ aryl groups and $C_5$-$C_{20}$ cycloalkyl groups. Examples of such substituents are linear or branched alkyl groups such as the methyl, ethyl, propyl, butyl, tert-butyl, pentyl and linear nonyl group. Other suitable organic groups are alkoxy groups, e.g. the methoxy and the ethoxy group; alkoxycarbonyl groups e.g. the methoxycarbonyl and the ethoxycarbonyl group and for instance a phenyl group. Particularly suitable are the alkyl groups that cause sterical hinder (bulky groups), for example isoalkyl groups, for example isopropyl, tert-butyl and neopentyl. However, other substituents such as electronegative groups are also suitable. Examples of electronegative groups are halogenide groups (—Cl, —Br, —F, —I), $C_1$-$C_6$ alkyl ester groups e.g. a methyl ester, a tert-butyl ester group and $C_5$-$C_{20}$ aryl ester groups e.g. phenyl ester, nitriles, ketone groups and sulphones.

$R^1$ and $R^2$ may also contain non-ortho-substituted substituents. These substituents may be the substituents referred to above.

A in formula (2) may be an n-valent group or an atom. Suitable atoms that may represent A are atoms chosen from Groups IVA, IVB, IIIA, IIIB and the lanthanides in the Periodic System of Elements (CAS version, Chemical and Engineering News, 63(5), 27, 1985), e.g. Si, B, Al and Ti (n equal to the valency of the atom). An n-valent group according to the invention is any group which can be bonded to two or more [—O—P($OR^1$)($OR^2$)]-groups. The group may be an organic or inorganic group. Organic groups e.g. polymers in which n is indefinitely large and macromolecules where n as a rule is greater than 8 are, for example, suitable as n-valent group A. Examples of polymers that are suitable for forming an n-valent group A are polyvinylalcohol and carbohydrates. Group A may also be an inorganic compound in which A represents, for instance, a carrier for a heterogeneous catalyst. Suitable inorganic groups A are, for instance, silica and zeolites.

Most preferably, A in formula (2) is an n-valent organic group with 1-30 carbon atoms in which n is 2-8. Examples of such ligands are the ligands according to formula's Ligand (1)-Ligand (8), in which t-Bu is a tert-butyl group, Me is a methyl group, $nC_9H_{19}$ is a linear nonyl group and OMe is a methoxy group.

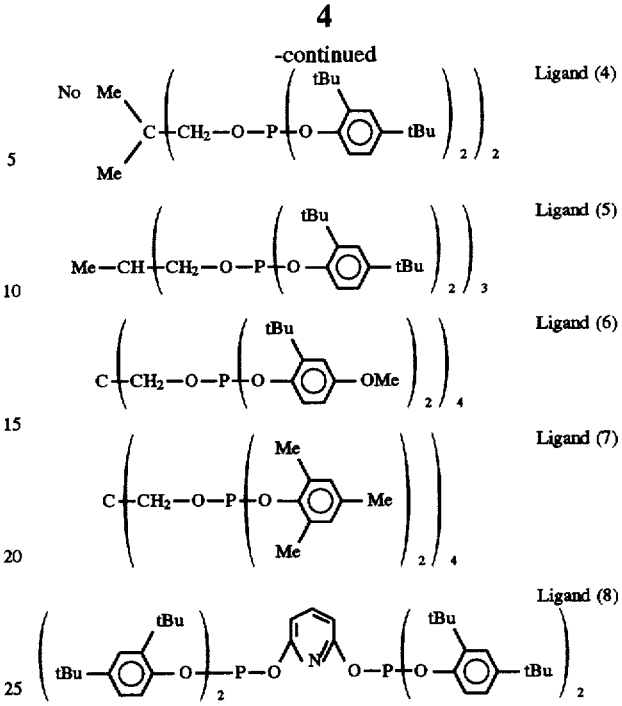

The phosphite compound used as ligand may with advantage be prepared in a two step synthesis. The synthesis may be performed in a single vessel (without purification of the intermediate product) in which process a phosphorus halogenide e.g. phosphorus trichloride is reacted with a hydroxyhydrocarbon compound which may be represented by the general formulae $R^1$—OH and $R^2$—OH. The reaction is effected in a solvent, e.g. toluene, in the presence of a hydrogen halogenide receptor, e.g. an amine, an intermediate product of the general formula Cl—P($OR^1$)($OR^2$) being prepared. The phosphite according to the invention is prepared in a second step by reacting this intermediate product with a hydroxyhydrocarbon of the general formula A—(OH)$_n$. The preparation of such phosphite compounds is also described in the aforementioned EP-A-518241.

As described above, it may be advantageous in the preparation of the phosphite according to the invention to start from an inorganic hydrocarbon compound with an amount of n hydroxy groups (n in formula 2). This compound forms the basis of the n-valent group A and the location of the hydroxy groups in the organic compound determines whether a phosphite is prepared that is capable of forming a chelate-type complex. Suitable phosphites that form a chelate-type complex may be prepared starting from, for instance, the following hydroxy groups-containing hydrocarbon compounds: 2,2-biphenyldiol, 2,2'-dihydroxydiphenylmethane, catechol, 1,2-cyclohexanediol, cis-1,2-cyclododecanediol, ethylene glycol, 1,3-propanediol, pentaerytritol, 1,1'-thiobis(2-naphthol),1,1'-dinaphthol, 2,3-dihydroxynaphthalene and 1,8-dihydroxynaphthalene.

Preferably, A is a C—(CH$_2$—)$_4$ group, in which n in formula (2) is equal to 4. Such a phosphite compound used as ligand can be prepared starting from the readily obtainable pentaerytritol. The resulting compounds will have a low cost price which is very advantageous. Especially when the small amounts of ligand decompose during the reaction and fresh ligand will have to be supplied to the catalyst system in order to maintain a reasonable reaction rate and/or selectivity.

The process according to the invention may start from 3-pentenoic acid in a process to prepare 5-formylvaleric acid

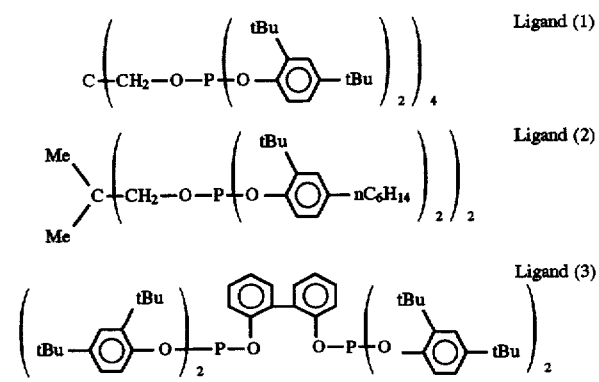

or from 3-pentenoate ester in a process to prepare 5-formylvalerate ester. Below the ester will be further described. The reaction conditions described below also apply to the acid.

The 3-pentenoate ester may be represented by the following general formula:

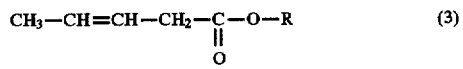 (3)

where R represents a (cyclo)alkyl group having from 1 to 8 carbon atoms or an aryl group or arylalkyl group having from 6 to 12 carbon atoms. Examples of these groups are the methyl, ethyl, propyl, isopropyl, n-butyl, tert-butyl, isobutyl, cyclohexyl, benzyl and the phenyl group. The methylester and ethylester are preferably applied. These esters can be prepared in a simple manner and with high selectivity starting from butadiene and methanol or ethanol.

The 3-pentenoate ester can be hydroformylated as a pure substrate or in a mixture of 3-pentenoate ester and other isomeric pentenoate esters. The other pentenoate esters are 4- and 2-pentenoate esters. Preferably the process is carried out starting with such a mixture of pentenoate esters because such mixtures are easy to prepare. For example these mixtures can be prepared by carbonylation of butadiene with carbon monoxide and an alcohol. The alcohol will correspond with the ester group R in formula (3) and can be represented by R—OH. Examples of possible processes to perform such a carbonylation of butadiene are described in U.S. Pat. No. 3,161,672, U.S. Pat. No. 3,253,018 and EP-A-301450. Processes to prepare mixtures of pentenoic acids are, for example, described in EP-A-284170 and EP-A-450577. As a rule, the 3-pentenoate ester (or acid) content in such a mixture is higher than 50%. Furthermore the reaction mixture will as a rule contain small amounts of 2- and 4-pentenoate ester when 3-pentenoate ester is reacted in a continuous process, in which unconverted pentenoate of the hydroformylation reaction is recycled to the hydroformylation zone for further reaction.

The linear 5-formylvalerate ester (or acid) prepared by the process according to the invention may serve as raw material for adipic acid, which compound is a raw material for Nylon-6,6 and for ε-caprolactam, which compound is a raw material for Nylon-6. ε-caprolactam may be prepared starting from a 5-formylvalerate ester by, for example, the process of U.S. Pat. No. 4730041. A comparable process to prepare ε-caprolactam starting from 5-formylvaleric acid is disclosed in EP-A-242505.

As a rule, the temperature of the hydroformylation is between 30° and 150° C. and preferably between 50° and 120° C. The pressure may be between 0.1 and 20 MPa. The pressure preferably is between 0.2 and 5.0 MPa.

As a rule a molar excess of bidentate phosphite compound relative to rhodium is used for the hydroformylation. The ratio of bidentate phosphite compound and rhodium (L/Rh, expressed in mol/mol) generally lies between 1:1–100:1. Preferably, this ratio lies between 1:1–50:1.

The $H_2$:CO molar ratio may lie between 1:10 and 10:1 and preferably between 1:2 and 5:1.

Rhodium may be applied in any one of a variety of forms. The manner in which rhodium is introduced into the reaction mixture is not critical. As a rule, the catalytically active complexes based on a rhodium precursor such as $Rh(CO)_2$(acac) (acac=acetylacetonate), $Rh_2O_3$, $Rh_4(CO)_{12}$, $Rh_6(CO)_{16}$, $Rh(NO_3)_2$, $Rh(OAc)_2$ (OAc=acetate) and the substituted triphenylphosphine are formed in the reaction mixture. $Rh(CO)_2$(acac) or $Rh(OAc)_2$ is preferably used as rhodium precursor inasmuch as these compounds are easily obtainable.

The 5-formylvalerate in the reaction mixture can be recovered by distillation. The bidentate phosphite compound, because of its high molecular weight, will be left behind in the liquid phase and, because of the high stability of the phosphite compound, will not be susceptible to degradation from the high distillation temperatures. In consequence, the 5-formylvalerate ester can be isolated from the reaction mixture and the catalyst in a simple manner.

As a rule, the hydroformylation is effected in the presence of a solvent. If desired, however, the hydroformylation may also be effected without a solvent.

Suitable solvents are organic solvents that are inert or solvents that do not disturb the reaction. Possible solvents are for instance the starting compound and the product of the process and compounds that are related to the product to be formed, such as by-products and particularly condensation products which may form during the hydroformylation. Other suitable solvents are saturated hydrocarbons such as naphthas, kerosine, mineral oil and cyclohexane and aromatics, ethers, ketones and nitriles such as toluene, benzene, xylene, texanol® (Union Carbide), diphenyl ether, tetrahydrofuran, cyclohexanone and benzonitrile.

The invention will be elucidated with the following non-limiting examples.

EXAMPLE I

A 150 ml Hastalloy-C steel autoclave (Parr) was filled under nitrogen with $Rh(CO)_2$(acac) (1.15 * $10^{-5}$ mol), phosphite corresponding with Ligand (1) (ligand/rhodium (L/Rh)=5 mol/mol) and 40 ml of toluene. Subsequently, the autoclave was sealed and purged with nitrogen. Next, the autoclave was heated to 90° C. in approx. 30 minutes and brought to a pressure of 1 MPa using carbon monoxide/ hydrogen (1:1 mol/mol). Thereafter, a substrate mixture (3.3 g of methyl 3-pentenoate, 1.0 gram of nonane made up with toluene to 10 ml) was injected into the autoclave. The composition of the reaction mixture was analysed by means of gas chromatography. The results are in table 1.

TABLE 1

| example | 3-MP/ Rh | time/ hours | conv./ % | 4-mp | cis + trans- 2-mp | mv | 3-fv | 4-fv | 5-fv |
|---|---|---|---|---|---|---|---|---|---|
| I | 1950 | 7 | 13.5 | 8.9 | 7.5 | 6.0 | 5.3 | 2.3 | 69.6 |
|  | 1950 | 25.5 | 45.3 | 2.0 | 6.7 | 7.0 | 4.5 | 2.1 | 77.5 |
| II | 15820 | 6.5 | 15.8 | 15.6 | 11.7 | 5.6 | 4.3 | 1.9 | 61.0 |
|  | 15820 | 27 | 54.2 | 1.2 | 5.7 | 5.4 | 5.2 | 2.0 | 80.4 | conv.=converted methyl 3-cis-pentenoate and methyl 3-trans-pentenoate (%)
4-mp=yield of methyl 4-pentenoate /conv. (mol %)
cis+trans-2-mp=yield of 2-cis-pentenoate and 2-trans-pentenoate/conv. (mol %)
mv=yield of methylvalerate/conv. (mol %)
4-fv=yield of methyl 4-formylvalerate/conv. (mol %)
5-fv=yield of methyl 5-formylvalerate/conv. (mol %)

EXAMPLE II

Example 1 was repeated using 20 ml of toluene (in place of 40 ml of toluene) and 27.1 grams of methyl 3-pentenoate.

Table 1 shows that the selectivity for methyl 5-formylvalerate (80.4 mol %) is distinctly better than in the prior art (EP-A-556681:76.7 mol %). In addition, the ratios of methyl 5-formylvalerate to methyl 3- and 4-formylvalerates (92:8 versus 85:15) are better. This and the fact that the unwanted isomeric formylesters substantially consist of methyl 3-formylvalerate facilitates distillative separation of the desired methyl 5-formylvalerate from the unwanted isomers (3-fv and 4-fv).

Comparative Experiment B

Example I was repeated using a phosphite of the following formula:

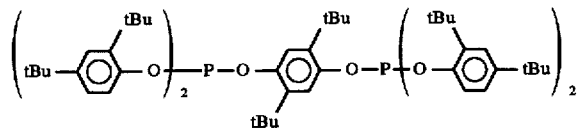

(phosphite No. 2 as used in EP-A-518241). The conversion was 56.9% after 1 hour. The following products had formed:

| | |
|---|---|
| methyl 4-pentenoate | 1.9 mol % |
| methyl 2-pentenoates | 30.5 mol % |
| methylvalerate | 3.8 mol % |
| methyl 3-formylvalerate | 12.5 mol % |
| methyl 4-formylvalerate | 27.7 mol % |
| methyl 5-formylvalerate | 23.6 mol % |

After 19.5 hours the conversion was 99.9%. The following products had formed

| | |
|---|---|
| methyl 2-pentenoates | 0.2 mol % |
| methylvalerate | 18.9 mol % |
| methyl 3-formylvalerate | 16.7 mol % |
| methyl 4-formylvalerate | 35.2 mol % |
| methyl 5-formylvalerate | 29.0 mol % |

This shows that non-chelate-type forming ligands such as the phosphite of this experiment are less suitable for preparing 5-formylvalerates with a high selectivity.

Comparative Experiment C

Example 1 was repeated using a phosphite of the following formula:

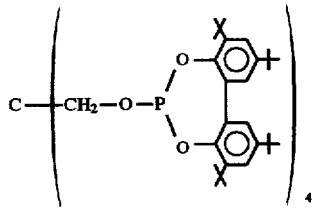

(which corresponds with phosphite No. XXV as used in EP-A-556681). After 6 hours the conversion was 13.6%. Refer to table 3 for the selectivities to the various products.

TABLE 2

| Time | 6 hours | 26 hours |
|---|---|---|
| Conversion | 13.6 | 48.3 |
| methyl 2-pentenoate | 12.0 | 10.4 |
| methyl 4-pentenoate | 4.6 | 1.3 |
| methylvalerate | 3.5 | 5.1 |
| methyl 3-valerate | 17.1 | 9.5 |
| methyl 4-formylvalerate | 19.9 | 21.9 |
| methyl 5-formylvalerate | 42.7 | 52.0 |

EXAMPLE III

Example I was repeated using the phosphite according to Ligand (2). The L/Rh was 4.9. The concentration of Rh was the same as in Example I. After 47 hours the conversion was 26.7%. The selectivity to methyl 5-formylvalerate was 63.4 mol % and with a n/b ratio of 2.8 (n/b is the ratio of linear 5-formylvalerate ester relative to the total amount of branched 3- and 4-formylvalerate esters).

EXAMPLE IV

Example I was repreated using the phosphite according to Ligand (3). The concentration of Rh was the same as in Example I. The L/Rh was 4.9. After 181 hours the conversion was 35.7%. The selectivity to methyl 5-formylvalerate was 75.8 mol % and with a n/b ratio of 6.1.

EXAMPLE V

Example I was repreated using the phosphite according to Ligand (4). The concentration of Rh was the same as in Example I. The L/Rh was 5. After 28 hours the conversion was 26.8%. The selectivity to methyl 5-formylvalerate was 65.8 mol % and with a n/b ratio of 4.4.

EXAMPLE VI

Example I was repreated using the phosphite according to Ligand (5). The concentration of Rh was the same as in Example I. The L/Rh was 5. After 44.5 hours the conversion was 43.9%. The selectivity to methyl 5-formylvalerate was 62.4 mol % and with a n/b ratio of 3.3.

EXAMPLE VII

Example I was repreated using the phosphite according to Ligand (6). The concentration of Rh was the same as in Example I. The L/Rh was 5. After 66 hours the conversion was 50.2%. The selectivity to methyl 5-formylvalerate was 71.1 mol % and with a n/b ratio of 6.4.

We claim:

1. Process for the preparation of 5-formylvaleric acid or the corresponding 5-formylvalerate ester by hydroformylation of 3-pentenoic acid or 3-pentenoate ester with carbon monoxide and hydrogen in the presence of a catalyst system comprising of rhodium and a phosphite ligand, characterized in that the phosphite ligand is represented by the following general formula

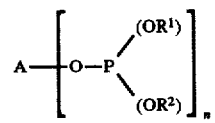

where $R^1$ and $R^2$ are the same or different monovalent aromatic organic groups and where A is an n-valent group or atom and where n is an integer of at least 2 and where the respective [—O—P(OR$^1$)(OR$^2$)] group may be the same group or different groups and where the phosphite forms a chelate-type complex with rhodium.

2. Process according to claim 1, characterized in that the organic group $R^1$ and $R^2$ is ortho-substituted with a group other than a hydrogen atom.

3. Process according to claim 2, characterized in that organic group $R^1$ and $R^2$ is substituted with a branched alkyl group having from 3 to 6 carbon atoms.

4. Process according to any one of claims 1–3, characterized in that $R^1$ and $R^2$, independently of one another, are a phenyl group or a β-naphthyl group.

5. Process according to any one of claims 1–4, characterized in that A is C—(CH$_2$—)$_4$.

6. Process according to any one of claims 1–5, characterized in that the 3-pentenoate ester is represented by the following general formula (2),

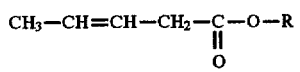
(2)
where R represents a (cyclo)alkyl group having from 1 to 8 carbon atoms or an aryl group or an arylalkyl group having from 6 to 12 carbon atoms.
7. Process according to any one of claims 1–6, characterized in that, besides the 3-pentenoate, an amount of 4- and 2-pentenoate is also present and that the concentration of 3-pentenoate ester is higher than 50%.
* * * * *

UNITED STATES PATENT AND TRADEMARK OFFICE
CERTIFICATE OF CORRECTION

PATENT NO. : 5,719,312
DATED : February 17, 1998
INVENTOR(S) : HANSEN et al.

It is certified that error appears in the above-identified patent and that said Letters Patent is hereby corrected as shown below:

Collumn 3, lines 56-60, please delete formula "Ligand 2" and replace same with

-- 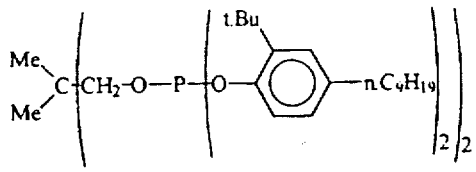 Ligand (2) --

Signed and Sealed this

Eighth Day of December, 1998

Attest:

BRUCE LEHMAN

*Attesting Officer*     *Commissioner of Patents and Trademarks*